United States Patent
Johnson aka Mindes

(10) Patent No.: US 7,389,873 B2
(45) Date of Patent: *Jun. 24, 2008

(54) POCKET-SIZED NEEDLE REMOVER AND RECEPTACLE

(76) Inventor: Evelyne Johnson aka Mindes, P.O. Box 24110, Los Angeles, CA (US) 90024

( * ) Notice: Subject to any disclaimer, the term of this patent is extended or adjusted under 35 U.S.C. 154(b) by 35 days.

This patent is subject to a terminal disclaimer.

(21) Appl. No.: 11/657,183

(22) Filed: Jan. 24, 2007

(65) Prior Publication Data

US 2007/0179443 A1 Aug. 2, 2007

Related U.S. Application Data

(60) Provisional application No. 60/763,334, filed on Jan. 30, 2006.

(51) Int. Cl.
*B65D 85/24* (2006.01)
(52) U.S. Cl. .......................... 206/366; 83/944
(58) Field of Classification Search ................ 206/364, 206/365, 366, 367, 370; 83/944
See application file for complete search history.

(56) References Cited

U.S. PATENT DOCUMENTS

| | | | |
|---|---|---|---|
| 3,585,835 A | * | 6/1971 | Clement ................. 72/260 |
| 3,683,733 A | | 8/1972 | Johan et al. |
| 4,255,996 A | | 3/1981 | Choksi et al. |
| 4,375,849 A | | 3/1983 | Hanifi |
| 4,404,881 A | * | 9/1983 | Hanifl ..................... 83/167 |
| 4,786,280 A | | 11/1988 | Maeda |
| 4,807,344 A | | 2/1989 | Kelson et al. |
| 4,969,379 A | * | 11/1990 | Taylor et al. ............. 83/167 |
| 4,989,307 A | | 2/1991 | Sharpe et al. |
| 5,092,462 A | | 3/1992 | Sagstettter et al. |
| 5,322,165 A | * | 6/1994 | Melker et al. ............ 206/366 |
| 5,761,975 A | * | 6/1998 | Waluda ..................... 82/58 |
| 6,880,701 B2 | | 4/2005 | Bergeron et al. |
| 2004/0065572 A1 | * | 4/2004 | Anthony et al. .......... 206/366 |

* cited by examiner

*Primary Examiner*—Jacob K Ackun, Jr.
(74) *Attorney, Agent, or Firm*—Lauson & Schewe LLP; Robert J. Lauson; Edward C. Schewe

(57) ABSTRACT

A device for severing syringe needles and storing the same for later disposal includes a lower box portion with a substantially flat bottom hinged to an upper lid portion, and a guillotine-like mechanism and an adjacent diaphragm spanning the two portions of an opposing side of the device. The guillotine preferably includes an angled blade in cross section such that when the needle is cut it is projected further through the diaphragm and into the device. The overall configuration and severing operation is in some ways akin to that of a stapler, in that a used syringe needle is inserted into a small gap between the two portions, and the top pushed down operating the guillotine to remove and retain the needle.

9 Claims, 2 Drawing Sheets

POCKET-SIZED NEEDLE REMOVER AND RECEPTACLE

CROSS-REFERENCE TO RELATED DOCUMENTS

This application is based on provisional application Ser. No. 60/763,334 filed Jan. 30, 2006.

BACKGROUND OF THE INVENTION

1. Field of the Invention

The present invention relates to safe disposal of syringe needles, and more particularly to a pocket-sized device that both cuts off and stores the needles and is disposable when full.

2. Description of the Related Art

Accidental needle sticks and re-use of disposable syringes, both which potentially spread serious diseases such as HIV and hepatitis B, are serious problems. In recognition thereof, U.S. regulations now mandate use of safety devises or needle removers with disposable syringes in hospitals. Syringes have been developed with capping mechanisms operable with one hand, or auto-disable features that withdraw the needle into the syringe barrel after use.

Additionally, there are needle removers that physically separate the needle from the syringe. With purchase of a single piece of equipment, users can safely dispose of many needles and prevent re-use of those syringes. The used syringe body can be disposed of in the regular trash receptacles without danger to those handling the trash.

Some electrically-powered devices either melt the needle or cut it away. These require electricity and must be plugged into the wall, however. A manually operated and portable device would be preferable. Most desirable would be a small, lightweight and simple device that would provide the necessary mechanical advantage to sever the needle with moderate pressure from one hand while at the same time easy for the user to carry around on his or her person and inexpensively priced.

OBJECTS OF THE INVENTION

Accordingly, it is an object of the present invention to provide a small, portable device to cut and retain used syringe needles.

It is a further object of the present invention to provide such a device that does not require electricity, batteries or any other external or internal power source.

It is a further object of the present invention to provide such a device that is easily and safely manually operable, configured to provide necessary mechanical advantage to sever the needles with the force of one hand.

It is a still further object of the present invention to provide a simple needle remover and receptacle that is very simple and inexpensive to manufacture and affordable.

It is a still further object of the present invention to provide such a device that includes disinfectant to render the captured needles non-infectious.

These and other objects and advantages of the present invention will become apparent upon reading the following detailed description and upon reference to the accompanying drawings.

SUMMARY OF THE INVENTION

A device for capturing used syringe needles for safe storage includes a receptacle or enclosure having a lower box portion and an upper lid portion movably connected thereto. Further, there is a guillotine-like mechanism and an adjacent diaphragm spanning the lower and upper portions of the receptacle. The needle of a disposable syringe after its use may be inserted into the guillotine and diaphragm, and the portions of the receptacle pushed together thereby cutting and retaining the needle.

Preferably the receptacle is constructed such that the two portions are hinged together at the rear side of the receptacle and the hinge is preferably spring loaded to bias the device in the open position. Also preferably the lower and upper portions separate only a sufficient distance at the front side to accommodate insertion of the syringe needle, and the bottom of the lower portion is substantially flat. The guillotine preferably includes an angled blade in cross section such that when the needle is cut it is projected rearward and through the diaphragm. Preferably the inside of the diaphragm is coated with disinfectant or there is other disinfectant material found in the box interior.

The method of removing and safely storing needles from used syringes includes providing a receptacle or enclosure having an opening between its sides and an inward-angled cutting surface attached to one of the sides and a diaphragm near the cutting surface inside the enclosure. The method also includes inserting a syringe needle between the mating cutting surfaces; and forcibly bringing the sides of the enclosure together thereby cutting the needle and propelling the needle through the diaphragm.

Preferably the bottom side of the enclosure is substantially flat, such that the step of forcibly bringing the sides together involves pushing down on the top of the enclosure with the bottom side bearing against a substantially flat surface, the sort of operation that is easily done with just a few fingers of one hand as the other hand is holding the syringe.

DESCRIPTION OF THE PREFERRED EMBODIMENT

Figure 1:
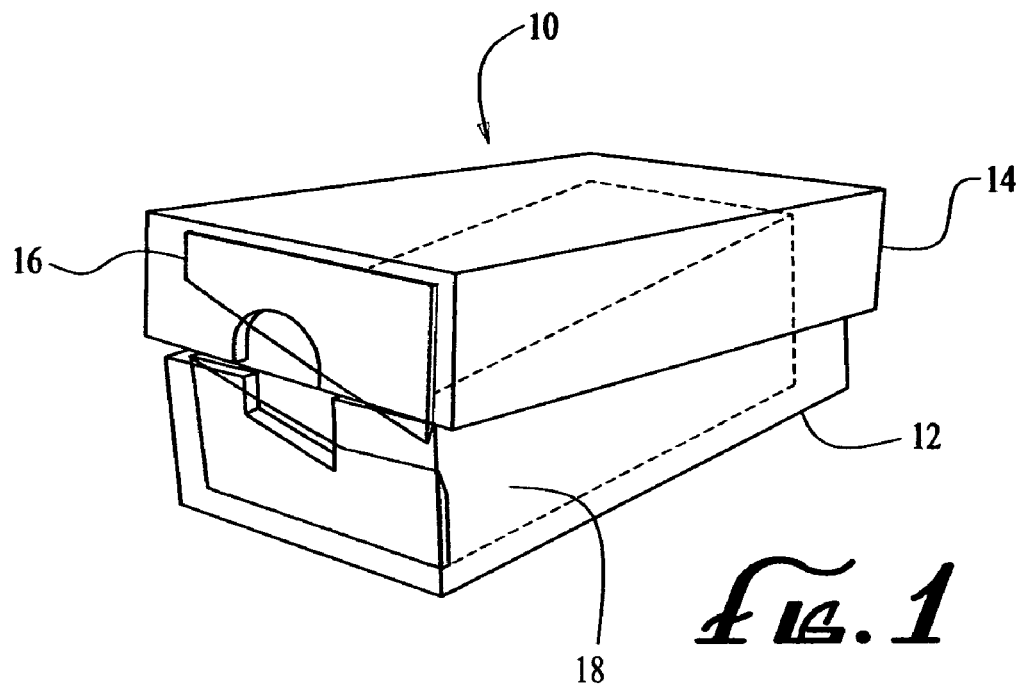
FIG. 1 is a perspective view of the pocket-sized needle remover and receptacle of the preferred embodiment of the present invention.
Figure 2:
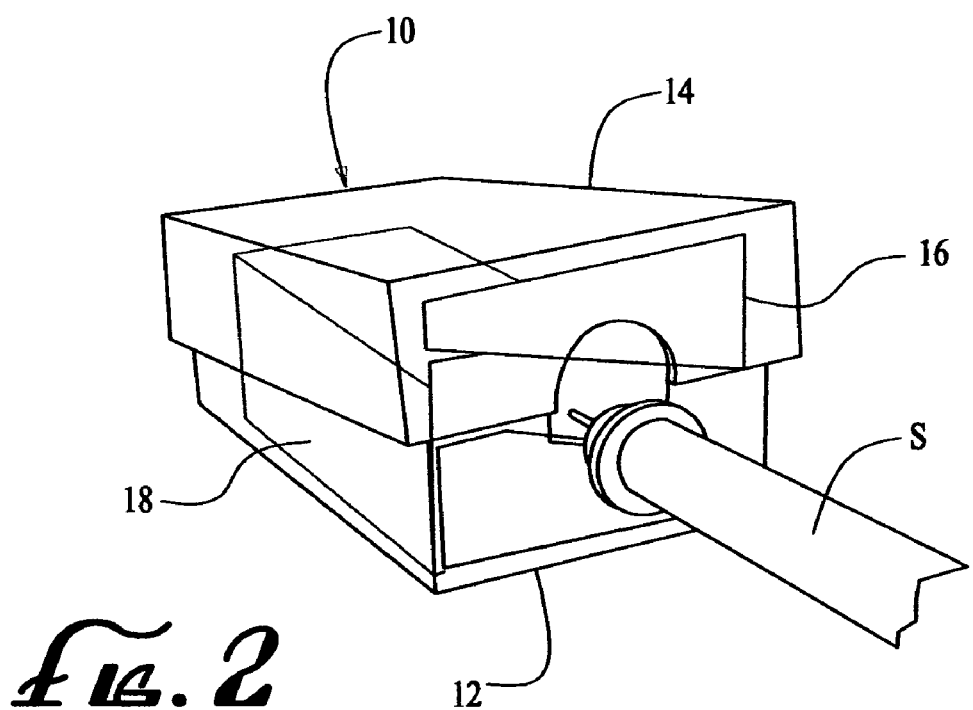
FIG. 2 is a perspective view thereof showing insertion of a syringe needle into the device.

First referring to FIGS. 1, 2, shown is a pocket-sized, combination needle remover and receptacle 10 of the preferred embodiment of the present invention. The device 10 includes a lower box portion 12 and an upper lid portion 14 that are moveably attached together as better shown in FIGS. 3, 4. A guillotine-like mechanism 16 spans the opening between the sides. Further, there is a diaphragm or permeable, rubbery membrane 18 behind the guillotine 16, preferably having a disinfectant coating 20 on its inside surface or other disinfectant material being found therein. A hinge 22 connects the lower 12 and upper 14 portions, and is preferably spring loaded to bias the device 10 in the open position. A conventional latch of some sort (not shown) would overcome the spring-loaded hinge 22 forces and hold the two portions 12, 14 of the device 12 together and closed when not in use. Importantly, note the upper blade of the guillotine 16 has an angled (in cross section) cutting surface 24. The device 10 is preferably made of a clear or translucent synthetic plastic material, and of a size that holds about a month's supply of used needles, probably about the size of a conventional small, flip-style cigarette lighter.

Figure 3:
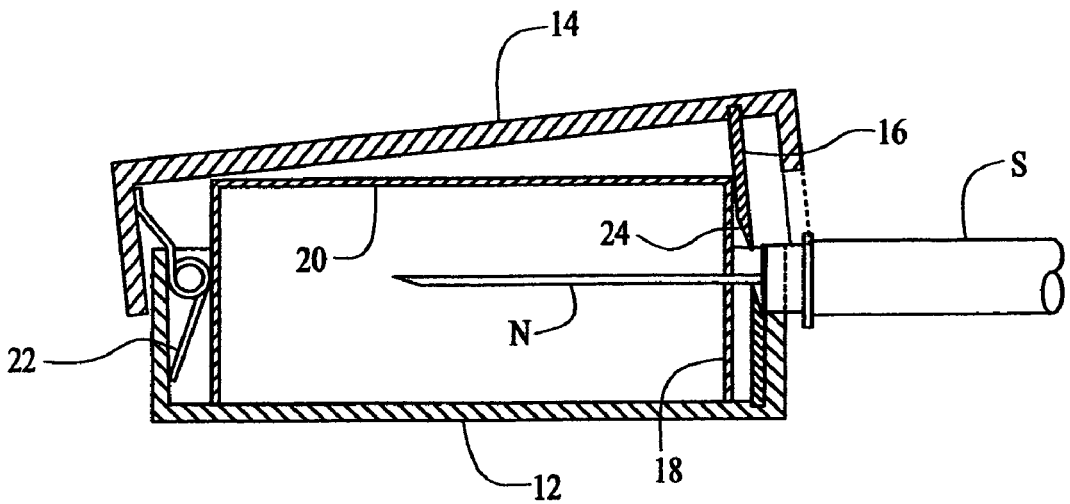
FIG. 3 is a side view thereof.
Figure 4:
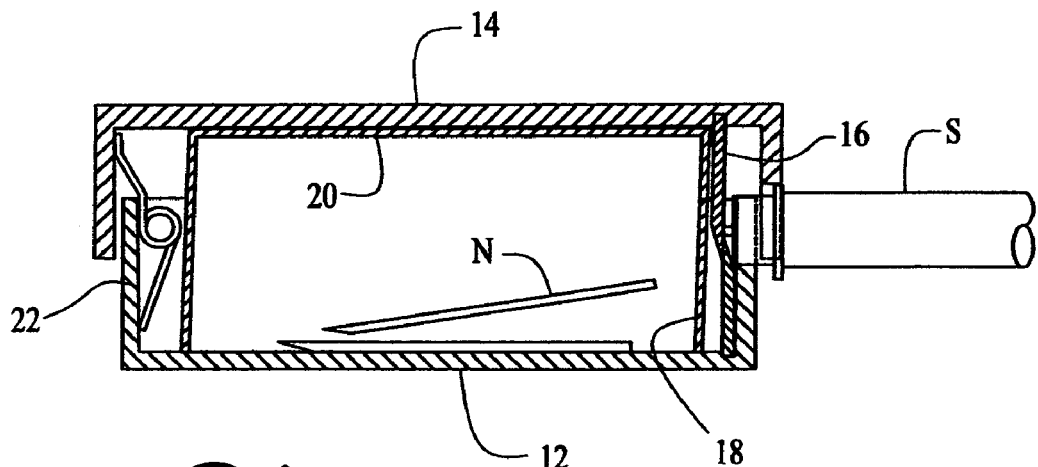
FIG. 4 is a view showing the needle being severed and propelled into the receptacle; and, FIG. 5 is a side view of the syringe after the needle was removed.
Figure 5:
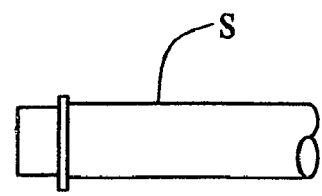

Having described the structure of the device 10, now referring primarily to FIGS. 3-5 its operation, function and use may be discussed. The device 10 should be handy and ready for use after an injection, the latch disengaged and the device 10 sprung open. A disposable syringe S immediately after use may be held in one hand and the needle portion N inserted between the lower box portion 12 and upper lid portion 14 and through the diaphragm 18. Then with a few fingers of the other hand the user merely firmly pushes down on the upper lid portion 14 thereby activating the guillotine 16 and bringing the angled cutting surface 24 into contact with the needle N. As the needle N is severed it is projected further through the diaphragm 18 and inside the device 10 and retained therein. Then the device 10 is closed and latched and put back into the user's pocket, purse or medication and supplies kit, etc.

While the present invention has been described with regards to particular embodiments, it is recognized that additional variations of the present invention may be devised without departing from the inventive concept.

What is claimed is:

1. A device for capturing used syringe needles for safe storage comprising:
    a lower box portion;
    an upper lid portion movably connected to the lower box portion;
    a guillotine spanning the lower box portion and upper lid portion;
    a diaphragm spanning the lower box portion and upper lid portion adjacent the guillotine,
    whereby a syringe needle after use may be inserted into the guillotine and the diaphragm and the upper lid portion and lower box portion moved together thereby cutting and retaining the needle.

2. The device of claim 1 wherein the lower box portion and upper lid portion are hingedly connected at one side of the receptacle.

3. The device of claim 2 wherein the lower box portion and the upper lid portion separate only a sufficient distance at an opposing side of the receptacle to accommodate insertion of the syringe needle.

4. The device of claim 3 wherein the guillotine comprises an angled blade in cross section such that the needle as cut is projected through the diaphragm and inside the receptacle.

5. The device of claim 2 wherein the hinge is spring loaded to bias the upper lid portion to an open position.

6. The device of claim 2 wherein the lower box portion has a bottom side that is substantially flat.

7. The device of claim 1 further comprising a disinfectant inside the lower box portion.

8. A method of removing and safely storing needles from used syringes comprising the steps of:
    providing a receptacle having sides forming an enclosure and an opening between the sides and an inward angled cutting surface attached to one of the sides and a diaphragm proximate the cutting surface inside the enclosure;
    inserting a syringe needle between the mating cutting surfaces; and
    forcibly bringing the sides of the enclosure together thereby cutting the needle and propelling the needle through the diaphragm.

9. The method of claim 8 wherein a bottom side of the enclosure is substantially flat, and the step of forcibly bringing the sides of the enclosure together involves pushing down on a top portion of the enclosure with the bottom side bearing against a substantially flat surface.

* * * * *